United States Patent
Kalpin

(10) Patent No.: US 9,047,708 B2
(45) Date of Patent: Jun. 2, 2015

(54) NEEDLE TO PORT TRAJECTORY INDICATOR

(71) Applicant: MEDTRONIC, INC., Minneapolis, MN (US)

(72) Inventor: Scott L. Kalpin, Harris, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/070,665

(22) Filed: Nov. 4, 2013

(65) Prior Publication Data

US 2014/0058327 A1    Feb. 27, 2014

Related U.S. Application Data

(62) Division of application No. 12/207,093, filed on Sep. 9, 2008, now Pat. No. 8,573,228.

(60) Provisional application No. 60/973,827, filed on Sep. 20, 2007.

(51) Int. Cl.
*A61B 19/00* (2006.01)
*G06T 11/20* (2006.01)
*A61B 17/34* (2006.01)
*A61M 5/142* (2006.01)
(Continued)

(52) U.S. Cl.
CPC ........... *G06T 11/206* (2013.01); *A61B 17/3403* (2013.01); *A61B 19/5225* (2013.01); *A61B 2019/448* (2013.01); *A61B 2019/507* (2013.01); *A61B 2019/5251* (2013.01); *A61M 5/14276* (2013.01); *A61M 2039/0238* (2013.01); *A61M 2205/3523* (2013.01); *A61M 2209/045* (2013.01); *A61M 5/427* (2013.01)

(58) Field of Classification Search
USPC ........... 128/901, 903; 607/39, 50, 62, 40, 55, 607/60; 604/17, 29, 30, 31, 32, 36
See application file for complete search history.

(56) References Cited

U.S. PATENT DOCUMENTS

| 4,432,146 A | 2/1984 | Klein |
| 5,117,825 A | 6/1992 | Grevious |
| 5,171,228 A | 12/1992 | McDonald |

(Continued)

FOREIGN PATENT DOCUMENTS

| EP | 723 783 | 7/1996 |
| EP | 1 832 254 | 9/2007 |

(Continued)

*Primary Examiner* — Scott Medway
(74) *Attorney, Agent, or Firm* — Mueting, Raasch & Gebhardt, P.A.

(57) ABSTRACT

A system includes (i) a needle for insertion into a port of an implantable infusion device, and (ii) a receiver apparatus having a port location signal receiver module capable of receiving a signal from the implantable infusion device regarding spatial orientation of the port. The system further includes a processor operably coupled to the receiver apparatus and capable of determining the orientation of the needle relative to the port based on the received signal. The system also includes a display operably coupled to the processor. The processor is configured to cause the display to graphically render trajectory of the needle relative to the port. The port is graphically rendered as a target structure having a reference area. The needle is graphically rendered as an object moveable relative to the target structure. Occupation of the reference area by the object indicates trajectory alignment of the port and the needle.

11 Claims, 15 Drawing Sheets

(51) Int. Cl.
*A61M 5/42* (2006.01)
*A61M 39/02* (2006.01)

(56) References Cited

U.S. PATENT DOCUMENTS

| | | |
|---|---|---|
| 5,346,470 A | 9/1994 | Hobbs |
| 5,375,596 A | 12/1994 | Twis |
| 5,592,939 A | 1/1997 | Martinelli |
| 5,617,857 A | 4/1997 | Chader |
| 5,913,820 A | 6/1999 | Bladen |
| 5,991,664 A | 11/1999 | Seligman |
| 6,009,878 A | 1/2000 | Weijand |
| 6,021,343 A | 2/2000 | Foley |
| 6,305,381 B1 | 10/2001 | Weijand |
| 6,332,089 B1 | 12/2001 | Acker |
| 6,423,029 B1 | 7/2002 | Elsberry |
| 6,473,652 B1 | 10/2002 | Sarwai |
| 6,666,085 B1 | 12/2003 | Lowe |
| 6,689,056 B1 | 2/2004 | Kilcoyne |
| 7,147,615 B2 | 12/2006 | Wariar |
| 7,191,013 B1 | 3/2007 | Miranda |
| 7,658,196 B2 | 2/2010 | Ferreri |
| 2004/0199220 A1 | 10/2004 | Cantlon |
| 2006/0278247 A1 | 12/2006 | Hunter |

FOREIGN PATENT DOCUMENTS

| | | |
|---|---|---|
| WO | 98/00060 | 1/1998 |
| WO | 2006/031490 | 3/2006 |

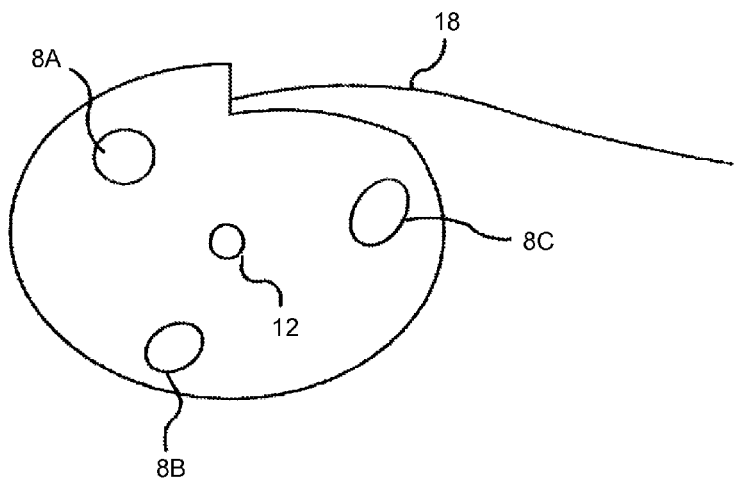
FIG. 2C
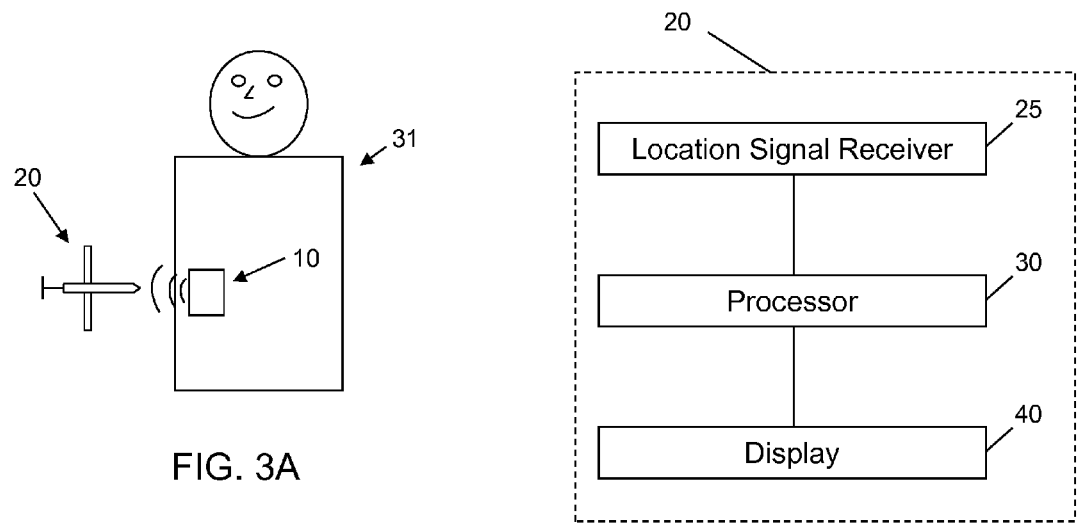
FIG. 3A
FIG. 4A

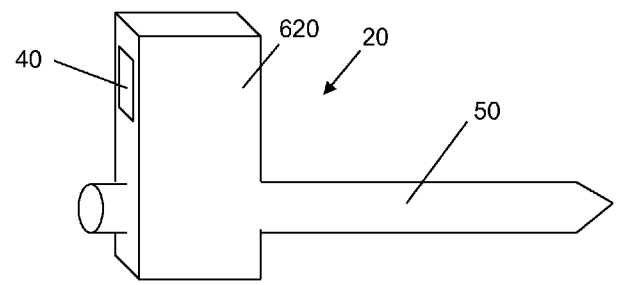
FIG. 8
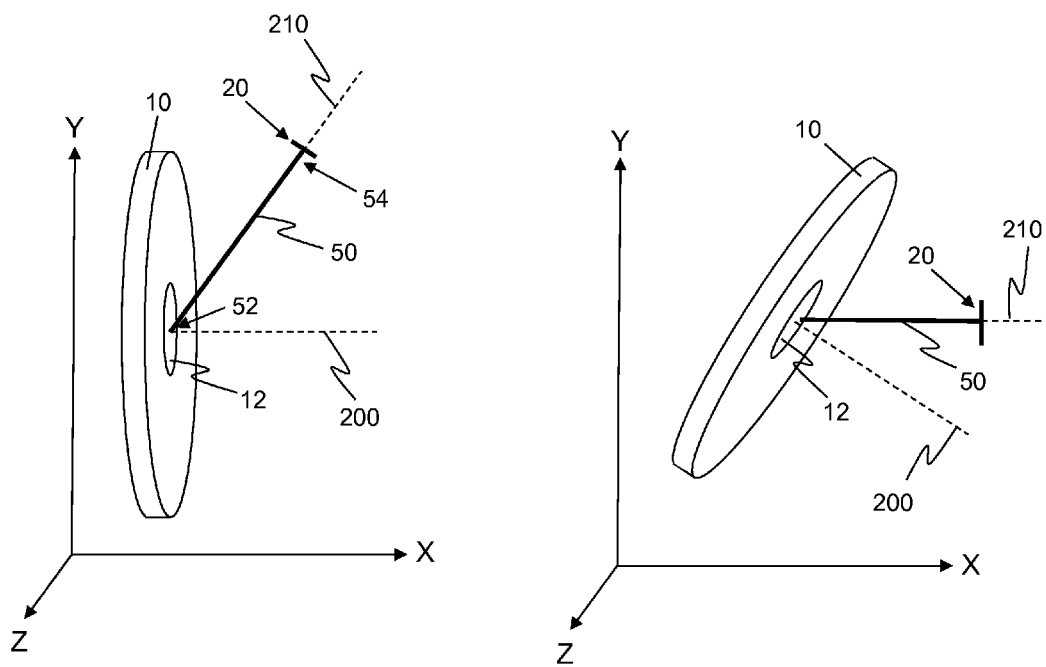
FIG. 9A
FIG. 9B

NEEDLE TO PORT TRAJECTORY INDICATOR

RELATED APPLICATION

This is a divisional application of U.S. patent application Ser. No. 12/207,093, filed Sep. 9, 2008, which issued on Nov. 5, 2013 as U.S. Pat. No. 8,573,228, and which claims the benefit of U.S. Provisional Patent Application No. 60/973,827 filed Sep. 20, 2007.

FIELD

This disclosure relates, inter alia, to implantable infusion devices, and more particularly to devices, systems and methods for percutaneously inserting needles in implanted infusion devices.

BACKGROUND

Implantable infusion devices, which can deliver low levels of therapeutic agents to target locations in patients, have been employed or contemplated for treating a variety of diseases. Such implantable infusion devices are often permanently implanted and may be used to periodically or continuously deliver the therapeutic agent. To ensure continued delivery of the therapeutic agent to the patient over time, reservoirs of such devices need to be replenished. Typically such replenishment is accomplished by inserting a needle though the patient's skin and through a septum covering a port in fluid communication with the reservoir.

Because such a device is implanted and thus not able to be directly seen, care must be taken to ensure that the needle is properly placed into the device before injection. If the needle misses the device and, in particular, misses the drug reservoir in the device, the drugs will be immediately dispensed in the body, having potentially dire consequences for the patient. Moreover, if the needle is not fully placed through the septum and into the drug reservoir, the drug reservoir will not be adequately filled, also having potentially dire consequences for the patient.

Port locator devices have previously been described. Such devices are intended to be placed on the patient's skin adjacent the implanted infusion device. A hole or opening in the port locator is positioned over the reservoir port. A needle may then be inserted through the hole in the port locator, through the patient's skin, and into the reservoir port. Some of such port locator devices are designed to determine not only the location of the port relative to the needle, but also the alignment of the needle relative to the orientation of the port.

However, when determining orientation or alignment, the user-interfaces of such devices tend not to be straight forward. Given the importance of proper alignment of a needle with a port of an implanted infusion device prior to insertion of the needle into the port, a more intuitive interface to indicate alignment is needed.

BRIEF SUMMARY

The present disclosure presents methods, systems, and devices that employ an intuitive graphical interface to depict the relative alignment of a needle with a port of an implantable infusion device. One example of an interface includes a graphical depiction of a two dimensional bubble style level indicator displaying trajectory error between desired and actual needle trajectory relative to the port.

In an embodiment, a system is described. The system includes (i) a needle for insertion into a port of an implantable infusion device, and (ii) a receiver apparatus having a port location signal receiver module capable of receiving a signal from the implantable infusion device regarding spatial orientation of the port. The system further includes a processor operably coupled to the receiver apparatus and capable of determining the orientation of the needle relative to the port based on the received signal. The system also includes a display operably coupled to the processor. The processor is configured to cause the display to graphically render trajectory of the needle relative to the port. The port is graphically rendered as a target structure having a reference area. The needle is graphically rendered as an object moveable relative to the target structure. Occupation of the reference area by the object indicates trajectory alignment of the port and the needle.

In an embodiment, a method is described. The method includes determining the orientation of a port of an implantable infusion device relative to a needle for insertion into the port. The method further includes displaying trajectory of the needle relative to the port by graphically rendering the port as a target structure having a reference area and by graphically rendering the needle as an object moveable relative to the target structure. Occupation of the reference area by the object indicates trajectory alignment of the port and the needle.

In an embodiment, a computer-readable medium is described. The computer-readable medium contains instructions that when implemented cause a needle alignment medical device system to (i) process information from a signal transmitted from an implantable infusion device regarding the location of a port of the infusion device, (ii) determine the orientation of a needle relative to the port based on the information from the transmitted signal, and (iii) graphically trajectory of the needle relative to the port. The port is graphically rendered as a target structure having a reference area. The needle is graphically rendered as an object moveable relative to the target structure. Occupation of the reference area by the object indicates trajectory alignment of the port and the needle.

By providing devices, systems and methods that employ an intuitive user interface to depict trajectory error between desired and actual trajectory of a needle relative to a port of an implantable infusion device, injection errors should be reduced. This and other advantages will be readily understood from the following detailed descriptions when read in conjunction with the accompanying drawings.

BRIEF DESCRIPTION OF THE DRAWINGS

FIGS. 2B-C are schematic diagrams of a top views of representative implantable infusion devices.

FIGS. 3A-C are schematic diagrams of representative systems in the environment of a patient.

FIGS. 4A-C are schematic block diagrams showing some components of representative systems.

FIG. 8 is a schematic perspective diagram of a representative needle apparatus having a display.

FIGS. 9A-B are schematic perspective views of representative implantable infusion devices.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure describes, inter alia, methods, systems and devices that employ an intuitive user interface to depict trajectory error between desired and actual trajectory of a needle relative to a port of an implantable infusion device. Improved accuracy and thus a reduction in injection errors should result.

The teachings of the present disclosure may be applied to any implantable infusion device having a port. The infusion device may be an active or passive infusion device. For example, the infusion device may contain a peristaltic pumping mechanism, a piston pump, an osmotic pump, or the like. The infusion device may be programmable, such as Medtronic's SYNCHROMED II infusion device.

Figure 1A:
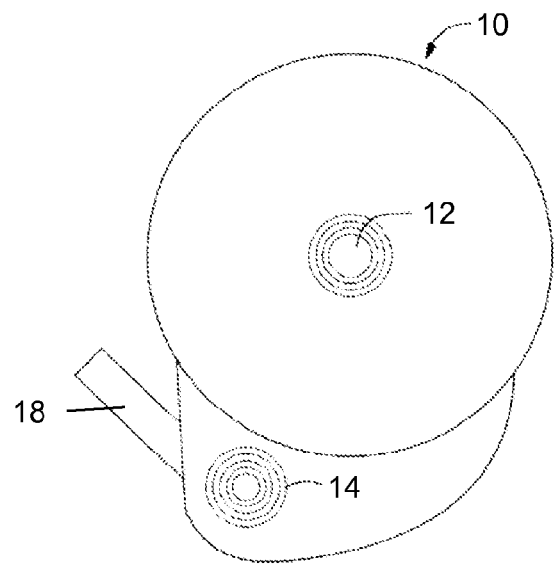
FIG. 1A is a schematic diagram of a top view of a representative implantable infusion device.
Figure 1B:
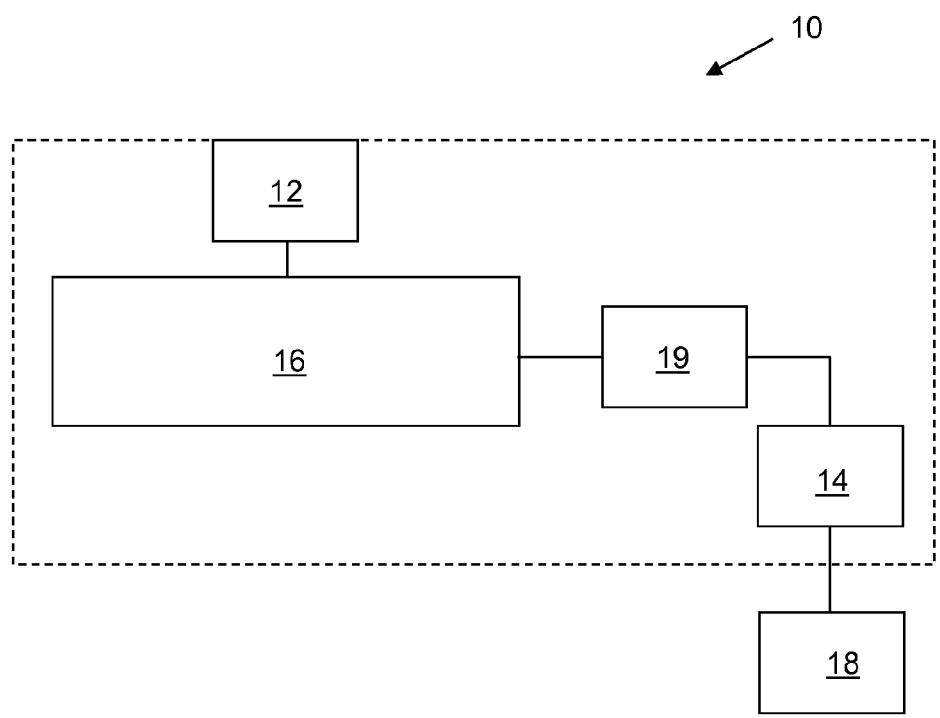
FIG. 1B is a schematic block diagram showing some components in a fluid flow path of a representative implantable infusion device.

Referring to FIGS. 1A-B, schematic diagrams of illustrative infusion devices 10 are shown. As shown in the top view of FIG. 1A, infusion device 10 may include a refill port 12 and a catheter access port 14. The refill port 12 is in fluid communication with reservoir 16 and allows entry of a needle for insertion or withdrawal of fluid to or from reservoir 16. Fluid flows from reservoir 16 to outlet catheter 18 to a desired location of a patient. In infusions devices 10 including both a refill port 12 and a catheter access port 14, catheter access port 14 is typically located downstream of reservoir 16 from refill port 12. Catheter access port allows for withdrawal of fluid from catheter 18 or insertion of fluid, such as a bolus drug delivery, into catheter 18. A one-way valve 19 may be positioned between reservoir 16 and catheter access port 14 to prevent withdrawal of fluid from reservoir 16 or infusion of fluid into reservoir 16 when fluid is withdrawn or infused into catheter access port 14.

Figure 2A:
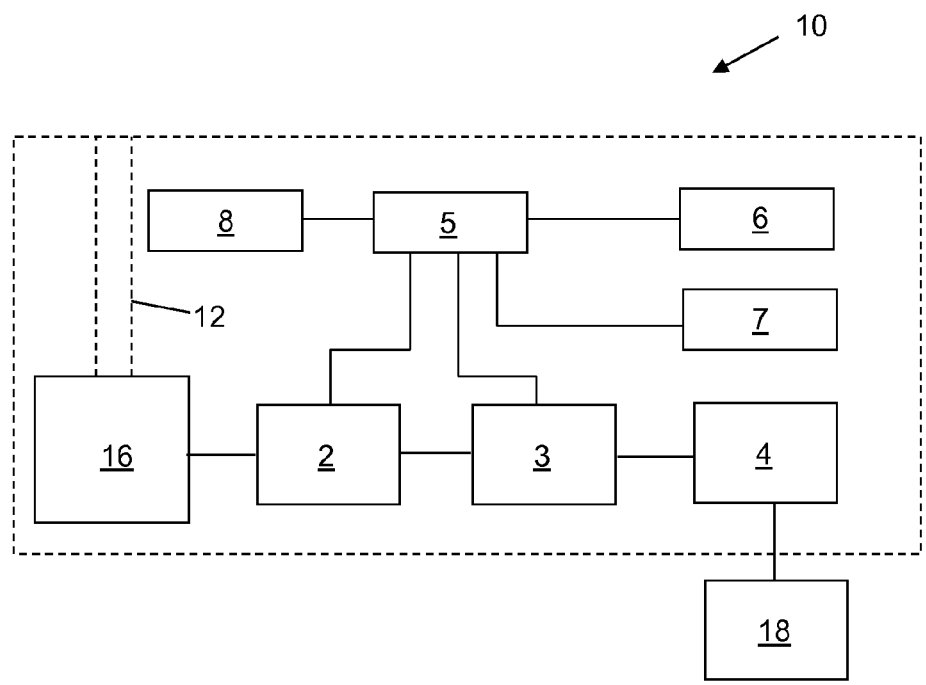
FIG. 2A is a schematic block diagram showing some components of a representative implantable infusion device.

Locating mechanisms, devices, user-interfaces or the like, as described in more detail below, may be employed with regard to any port of an implantable infusion device 10. However for the sake of clarity and convenience, such locating mechanisms, devices, user-interfaces will be described herein with regard to refill port 12. Referring to FIG. 2A, a block diagram of an embodiment of an infusion device 10 capable of generating a signal regarding the location of the refill port 12 is shown. In the depicted embodiment, a safety valve 2 is located between reservoir 16 and pump 3, and a flow restrictor 4 is located between pump 3 and catheter 18. However, it will be understood that any suitable fluid pathway and associated components may be employed with the teachings herein. Safety valve 2 and pump 3, in the depicted embodiment, are operably coupled to electronics 5. Electronics 5 can control the operation of, and provide power to (as appropriate), valve 2 and pump 3. Electronics 5 are operably coupled to power source 6 and to telemetry module 7 in the depicted embodiment. Telemetry module 7 provides for communication between implantable device 10 and an external device, such as a programmer. While module 7 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Electronics 5 are further operably coupled to, and may control operation of and provide power to, port location signaling module 8. Port location signaling module 8 may include any suitable components capable of generating a signal detectable by an external device. The external device, or a device operably coupled to the external device, may derive the location of the port 12 based on the signal. For example, port location signaling module 8 may include components described in U.S. Pat. No. 6,305,381, entitled "System for locating implantable medical device", issued on Oct. 23, 2001, which patent is hereby incorporated herein by reference to the extent that it does not conflict with the disclosure presented herein.

Figure 2B:
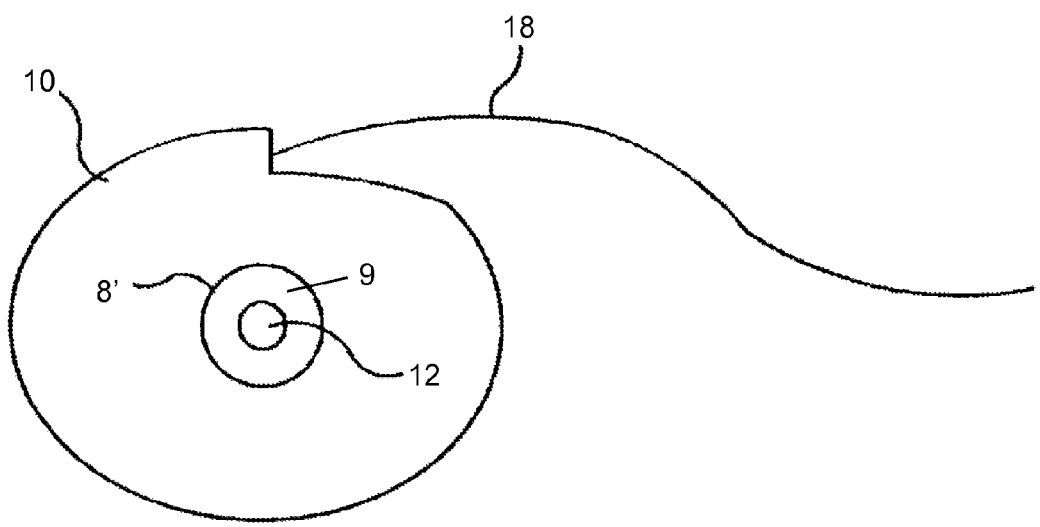

Referring to FIG. 2B, port location signaling module may include a coil 8' having an opening 9 coaxially aligned with port 12. Although port locating signaling module 8 is shown in FIG. 2A as a separate module, it should be appreciated that coil 8' may be fashioned by using a telemetry or recharge coil of the device 10. In the embodiment depicted in FIG. 2C, port locating signaling module includes a plurality of coils 8A, 8B, and 8C. Such a plurality of coils 8A, 8B, 8C may be used to each emit at a differing frequencies, or other suitable parameter, so that the external device may accurately sense the location of the port 12 in addition to the proper orientation of the external device relative to the implantable infusion device 10, which is discussed in more detail below.

Figure 3B:
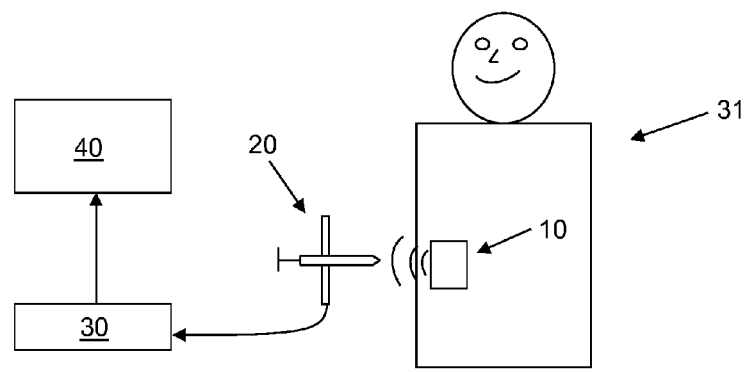
Figure 4B:
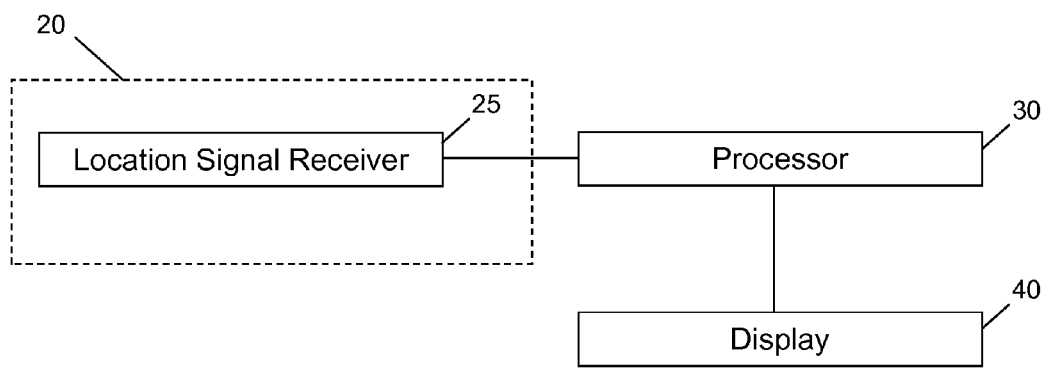
Figure 3C:
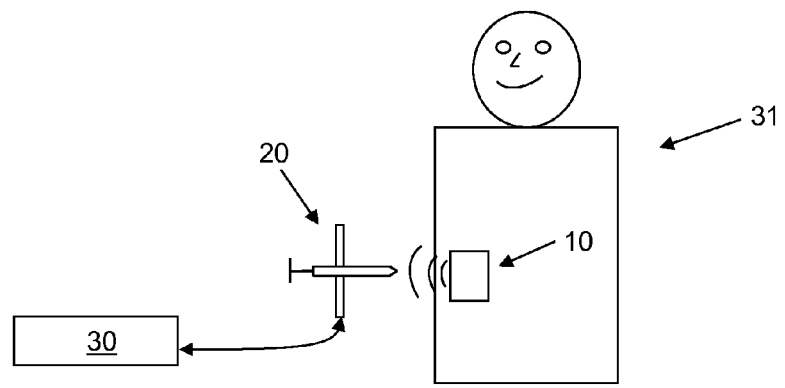
Figure 4C:
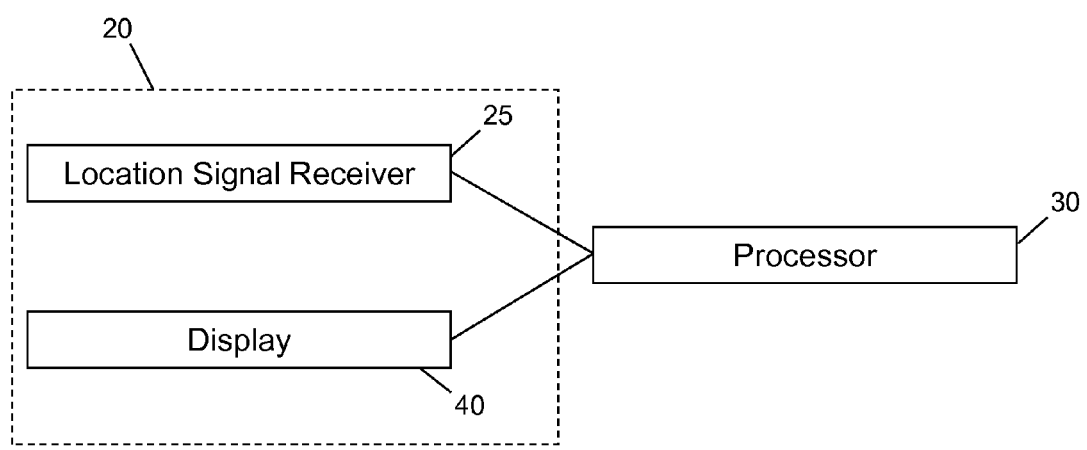

Referring now to FIGS. 3A-C, an implanted infusion device 10, via port location signaling module, emits signal through the skin of a patient 31. An external needle apparatus 20 detects signal from implanted device 10 and determines location or location and orientation of the implanted port, allowing for accurate infusion or withdrawal of fluid from implanted infusion device 10. Needle apparatus 20 may be self-contained, i.e., apparatus 20 may contain all components necessary or desired for proper location or alignment of apparatus 20 with the port of implanted device 10, or may be operably coupled (e.g., wirelessly or via wires) to additional components that may facilitate location of, and alignment with, a port of the implanted device 10. Such components include a location signal receiver module 25, a processor 30 for determining the relative location or alignment of the needle apparatus 20 to the port of the implanted device 10, and a display 40 for providing a user of the needle apparatus with an indication of the relative location and alignment of needle apparatus 20 and port of implanted device 10 (see, e.g., FIGS. 4A-C).

Location signal receiver module 25 is contained within or about needle apparatus 20 or a portion thereof and contains one or more components for detecting the signal transmitted from the port locating signal module of the implanted device 10. It will be understood that components of location signal receiver module will vary according to the type of signal transmitted from the implanted device 10. By way of example, and referring to FIG. 5A, location signal receiving module of needle apparatus 20 may include a plurality of sensing arrays 26-A, 26-B, 26-C, 27-A, 27-B, 27-C, 28-A, 28-B, 28-C of antennas, each series attuned to sense the output of a corresponding coil 8A, 8B, 8C (see, e.g., FIG. 2C) of port locating signaling module of implantable infusion device 10.

Figure 5A:
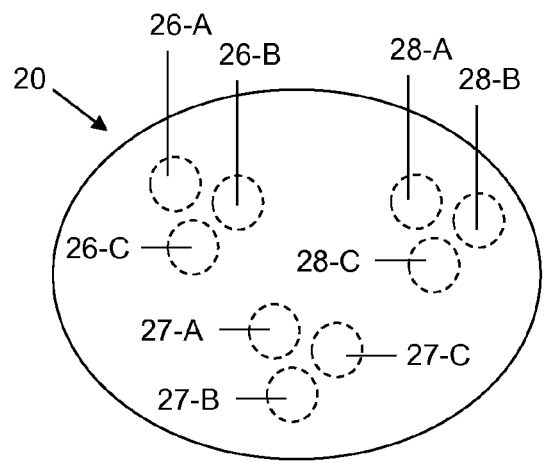
FIG. 5A is a diagrammatic illustration of a schematic view of a representative needle apparatus.
Figure 5B:
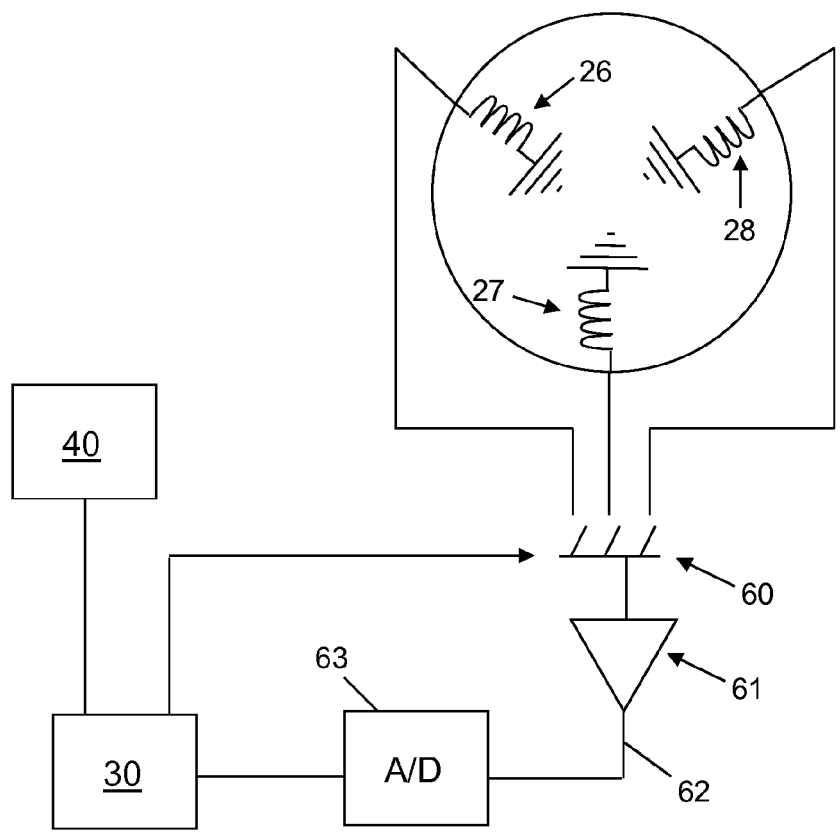
FIG. 5B is a schematic circuit and block diagram that may be used in conjunction with the needle apparatus depicted in FIG. 5A.

FIG. 5B depicts an embodiment of a circuit that may be used with a needle apparatus 20 depicted in FIG. 5A. As seen, antennas 26, 27 and 28 of the location signal receiver module are coupled to processor 30 through switch 60. Through such a coupling this embodiment uses a sampling technique to alternatingly sample the signal on each antenna. Each such sampled signal is then passed through amplifier 61 which also provides a filtering function and outputs the signal on line 62 as an RSSI. The signal is then processed through analog to digital converter 63 where it is then put into the processor 30. Processor 30 compares each of the signals sampled from the antennas. Processor 30 may then determine whether the same amount of energy is being sensed by each antenna, which, due to the geometry of implant coils 8A, 8B, 8C and the antennas 26, 27, 28 of the needle apparatus 20, indicates alignment, in this case both X,Y alignment and angle alignment, of the needle of the needle apparatus 20 and the port of the implanteable infusion device 10. Processor 30 may be operably coupled to a display 40 and cause a visual representation of the relative angular alignment or position of needle of needle apparatus 20 and port of infusion device 10 to be displayed, allowing user to adjust the position of needle apparatus accordingly. In an alternate embodiment, the system could also use a technique in which each coil is oppositely coupled, that is in anti-phase, such that when a null is sensed the coils are each sensing an equal amount of energy, rather than using a sampling technique to detect the energy sensed by each antenna (see, e.g., U.S. Pat. No. 6,305,381 for more detail). Of course, any suitable sensing combination of port locating signaling module of infusion device and location signal receiver module of needle apparatus may be employed.

Referring back to FIGS. 3A-C and 4A-C, needle apparatus 20 may be a self contained system and may include location signal receiver module 25, processor 30, and display 40 (see FIGS. 3A and 4A). Alternative configurations are also possible where one or more system components are external to needle apparatus 20. For example, and referring to FIGS. 3B-C and 4B-C, location signal receiver module 25 disposed in, on or about needle apparatus 20 may send information, either via cables or wirelessly, to processor 30. Based on the received information, processor 30 may then determine the relative orientation of needle of needle apparatus 20 and port of infusion device 10. Information regarding the relative positions of the needle of needle apparatus 20 and the port of infusion device 10 may then be displayed on display 40. In the embodiments depicted in FIGS. 3B and 4B, display 40 is external to needle apparatus 20. In the embodiments depicted in FIGS. 3C and 4C, display 40 is a component of the needle apparatus 20.

Figure 6A:
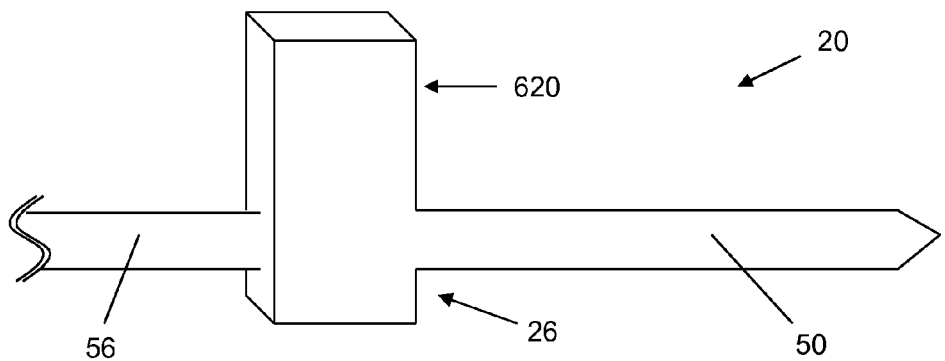
FIGS. 6A-C are schematic perspective diagrams of representative needle apparatuses.
Figure 6B:
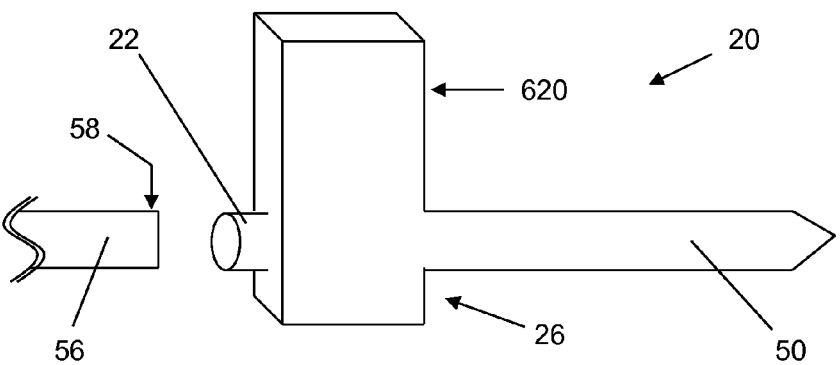
Figure 6C:
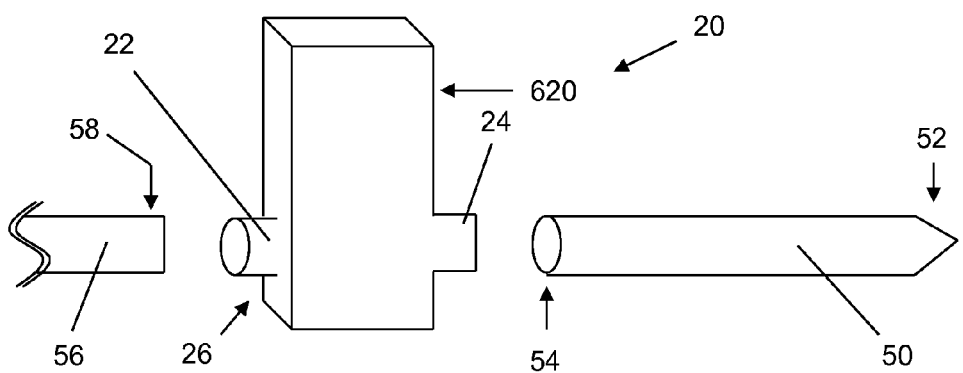

Referring now to FIGS. 6A-C, perspective views of illustrative needle apparatuses are shown. Needle apparatus 20 includes a needle anchoring portion 26 configured to axially fix the apparatus 20 relative to the needle 50. Needle apparatus 20 also includes a port locating portion 620 fixable relative to the needle anchoring portion 26. It will be understood that, as used herein, "fixable" and the like includes permanently affixed, detachable fixable and the like. Port locating portion 620 houses location signal receiver module 25 (see, e.g., FIGS. 4A-C) and may include processor 30, display 40 and any other necessary or desirable electronics, such as a power supply, digitizing electronics, or the like. Of course, as discussed above (e.g., with regard to FIGS. 4A and C), processor 30 or display 40 may be housed external to port locating portion 620 of needle apparatus 20. In the embodiment depicted in FIG. 6A, needle apparatus 20 includes needle 50 and tubing 56 or syringe or the like. In the embodiment shown in FIG. 6B, needle apparatus 20 includes needle 50 and includes a distal end portion 22 configured to fluidly couple to proximal end portion 58 of tubing 56 or syringe or the like. In the embodiment depicted in FIG. 6C, needle apparatus 20 serves as an adaptor configured to operably couple needle 50 to tubing 56 or syringe or the like. Needle apparatus 20 includes a proximal end portion 24 configured to axially fix needle anchoring portion 26 to proximal portion 54 of needle 50. Any suitable mechanism or connector may be used to axially fix needle anchoring portion 26 to needle 50.

Figure 7A:
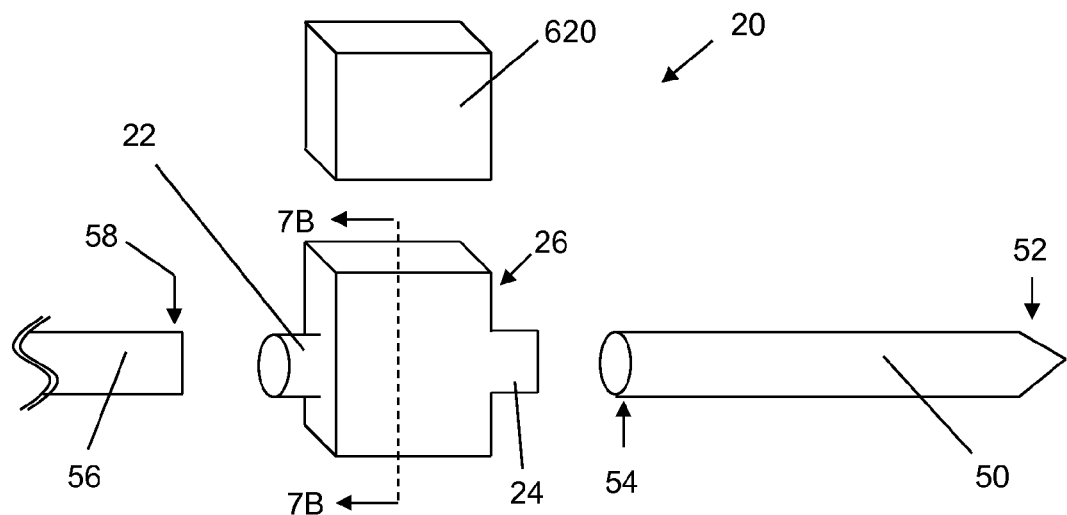
FIG. 7A is a schematic perspective diagram of a representative needle apparatus.

Referring to FIG. 7A, needle apparatus 20 may include a detachable port locating portion 620. Port locating portion 620 may be detachable in any manner, so long as it is fixable relative to needle anchoring portion 26 when in use. Having port locating portion 620 be detachable may be desirable, as needle anchoring portion 26 can be manufactured with little or no electronic components and be disposable. Removable port locating portion 620 which contains electronics (at least location signal receiver component electronics) may then be reusable.

Figure 7B:
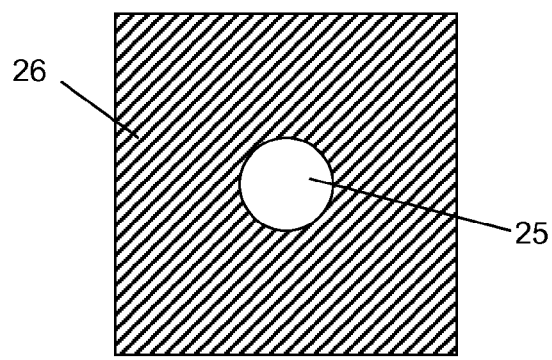
FIG. 7B is a schematic cross section taken along the line 7B-7B of the needle apparatus depicted in FIG. 7A.

In the embodiment depicted in FIG. 7A, needle anchoring portion 26 has a proximal end portion 24, a distal end portion 22, and a lumen 25 (see, FIG. 7B, which shows a cross section through line 7B-7B of FIG. 7A) extending through the needle anchoring element from the proximal end portion 24 to the distal end portion 22. The lumen 25 is configured to be fluidly coupled with a lumen of the needle 50 and a lumen of the tubing 56 or syringe or the like. Of course needle anchoring portion 26 need not contain a lumen 25 configured to be fluidly coupled with the lumen to the needle 50 and may be axially fixed about an exterior surface of the needle 50 or otherwise axially fixed relative to needle 50.

Any suitable mechanism for axially fixing needle anchoring portion 26 relative to needle 50 may be employed. By way of example, luer connections are used to axially secure needle anchoring portion 26 relative to needle 50. Additional information regarding needle apparatuses is provided in U.S. Provisional Application Ser. No. 60/973,824, entitled "Apparatus for Aligning Needle with Port of Infusion Device", having attorney docket no. 30062.00, and filed on Sep. 20, 2007, which provisional patent application is hereby incorporated herein by reference in its entirety to the extent that it does not conflict with the disclosure presented herein.

In various embodiments, needle apparatus 20 may include a display 40 for indicating the relative position or orientation of needle 50 relative to a port of an implantable infusion device. One such embodiment is depicted in FIG. 8, where display 40 is disposed on or exposed through an external surface of port locating portion 620. Any suitable display 40, such as a LCD display, a series of LEDs, or the like, may be used.

For the processor to accurately calculate the angular orientation and relative position of the needle to the targeted port and cause display 40 to render an accurate image of the relative position or orientation, the relative position of the port location signal receiver 25 to the needle 50 should be taken into account. For example, and referring back to FIGS. 6A-C, port locating portion 620 houses the port location signal receiver 25. In the embodiments, depicted in FIGS. 6A-C, the port locating portion 620 is off center from needle 50. Accordingly, the position of the port location signal receiver 25 is off center from the needle. Information regarding the distance from axial center of the needle 50 and the distance along the length of the needle from the tip 52 to the port locating portion 620 may be accounted for in making a determination of the relative positions of needle 50 and the target port.

With regard to the discussion that follows, reference will be made to needle 50; however, it will be understood that needle 50 may be a part of or included in a needle apparatus 20. In addition, it will be understood that the discussion that follows will be applicable to devices and systems that incorporate a port location signal receiver 25 axially fixed relative to needle 50 or otherwise positioned, so long as a processor 30 can obtain information regarding the relative alignment of needle 50 with port 12.

Referring now to FIGS. 9A-B, perspective views of implantable infusion devices are shown and illustrate the importance of alignment of a needle 50 with a port 12. In the figures, a desired alignment axis 200 of the port 12 is depicted and actual needle axis 210 of needle 50 is shown to be out of alignment with desired axis 200. If needle 50 is out of alignment, even though the proximal tip 52 of needle 50 is properly located as shown, injection or fluid withdrawal error may occur. Accordingly, proper alignment of actual needle axis 210 and desired needle axis 200 is important. As infusion device 10 is subcutaneously implanted and cannot be seen during procedures where needle 50 is to be inserted into port 12, a suitable mechanism for determining alignment of needle 50 with port 12 is desired.

It will be understood that the components and devices described in FIGS. 1-9 are but examples of components and devices that may be employed to detect relative orientation of a needle and a targeted port and that many other device or system configurations may be employed to generate a user-interface as described with regards to FIGS. 10-13. However, for the sake of convenience, the discussion that follows with regard to FIGS. 10-13 will refer to components as described with regard to FIGS. 1-9.

A receiver apparatus, such as a needle apparatus 20, including a port location signal receiver module 25 capable of receiving a signal from an implantable infusion device 10 regarding the spatial orientation of a port 12 of the device 10 may be operably coupled to a processor 30. The processor 30 may be operably coupled to the display 40. The processor 30 may be configured to cause the display 40 to graphically render relative alignment of the needle 50, or actual needle axis 210, to the port 12, or desired needle axis 200. It will be understood that appropriate desired or required components, such as digitizing electronics, may be employed so that processor 30 may cause display 40 to render the graphical depiction.

Figure 10A:
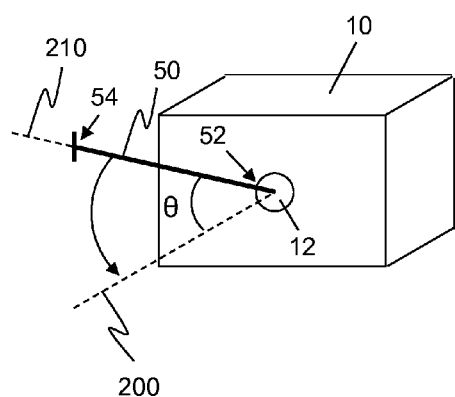
FIGS. 10A, C, and E are schematic perspective views of representative implantable infusion devices.
Figure 10B:
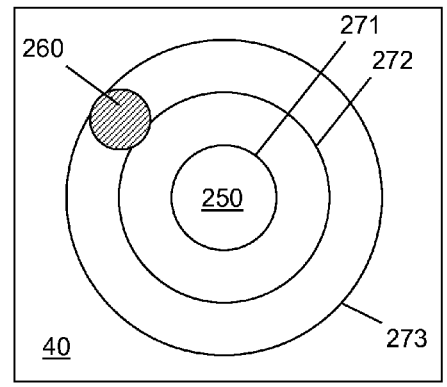
FIGS. 10B, D, and F are schematic front views of a display graphically rendering a representative alignment of a needle with a port of an implantable infusion device.
Figure 10C:
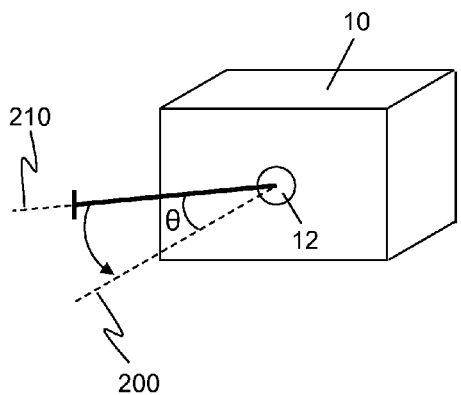

An example of an embodiment of a graphical rendering is shown in FIGS. 10B, D, and F, with reference made to FIGS. 10A, C, and E for the purposes of illustration. In the illustrative graphical rendering, the port 12 is graphically rendered as a target structure having a reference area 250, and needle 50 is graphically rendered as an object 260 moveable relative to the target structure. The port target structure may alternatively be considered to represent the desired needle axis 200 and the needle object 260 may alternatively be considered to represent the actual needle axis 210. In the embodiments depicted in 10B, D, and F, reference area 250 is defined by a first target trajectory reticule 271. Second 272 and third 273 target trajectory reticules are also shown as concentric circles about the center of the first circular reticule 271. Of course reticules make take any desirable or suitable shape and may be in any desired number. In the depicted embodiment, the reticules 271, 272, 273 demarcate defined tilt errors; i.e., the angle of error of actual needle trajectory axis 210 to desired trajectory axis 200. In various embodiments, the pitch error may be displayed on the vertical axis, and the yaw error may be displayed on the horizontal axis.

Figure 10D:
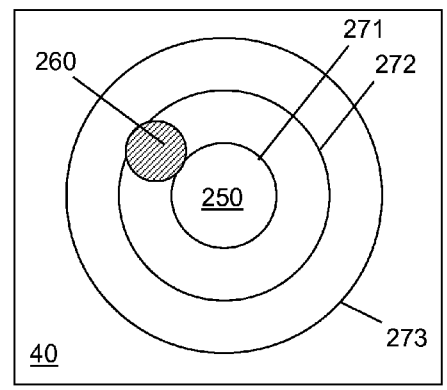
Figure 10E:
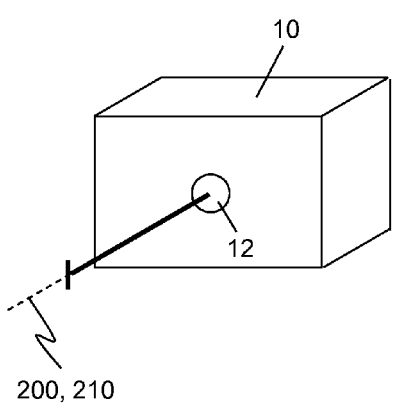
Figure 10F:
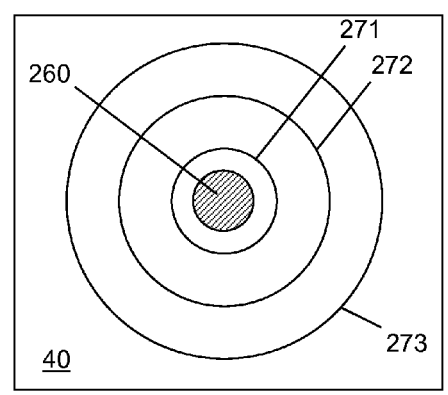

Referring now to FIG. 10A, proximal portion 52 of needle 50 is shown as being positioned over port 12, but actual needle trajectory 210 is out of alignment with desired needle trajectory 200 by angle θ due to distal portion of needle 50 being out of desired position. As shown in corresponding FIG. 10B, object 260, representing actual needle trajectory 210 relative to desired trajectory 200, is depicted generally between second 272 and third 273 target trajectory reticules. By way of example, the second target trajectory reticule 272 may represent five degrees of tilt error and the third reticule 273 may represent ten degrees of tilt error. Accordingly, the area between the second 272 and third 273 target trajectory reticule would represent between 5 and 10 degrees of tilt error. Moving the distal portion 54 of needle 50 in the direction indicated by object 260, without moving proximal portion 52 of needle 50 results in reduced tilt error, as shown the reduced angle θ shown in FIG. 10B. As needle 50 is moved and thus, as needle axis 210 changes, display 40 may be updated, preferably in real time or near real time. As shown in FIG. 10D, movement of needle 50 to the position depicted in FIG. 10C, resulted in object 260 moving in the target area between the first 271 and second 272 reticules. In the depicted embodiment, first reticule may represent, for example, two degrees of tilt error. Further movement of distal portion 54 of needle 50 results in alignment of needle trajectory 210 with desired trajectory 200 as shown in FIG. 10E. As shown in corresponding FIG. 10F, object 260 then occupies reference area 260 indicating alignment of needle 50 with port 12. The degree of tilt error represented by reticules 271, 272, and 273 may be any desirable tilt error. It will be understood that the degree of acceptable tilt error will vary from device to device and may be 2 degrees in some systems, e.g. as discussed above with regard to first reticule 271 that defines reference area 250, may be one degree with other systems, 5 degrees with other systems, 10 degrees with other systems, etc. In an embodiment, the first reticule 271 defines a tilt error of about 5 degrees and the second reticule 272 defines an error of about 10 degrees.

Figure 11A:
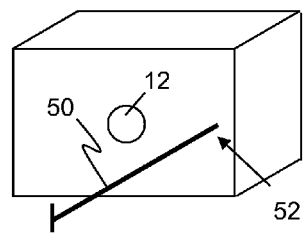
FIGS. 11A, C, and E are schematic perspective views of representative implantable infusion devices.
Figure 11B:
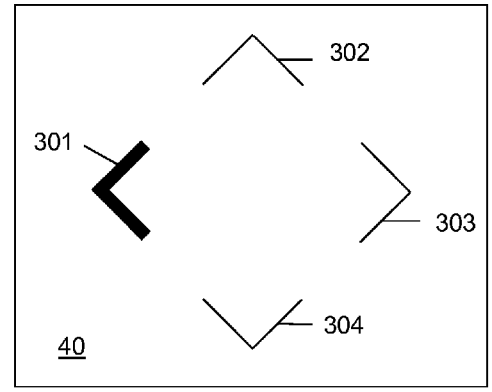
FIGS. 11B, D, and F are schematic front views of a display graphically rendering a representative alignment of a needle with a port of an implantable infusion device.
Figure 11C:
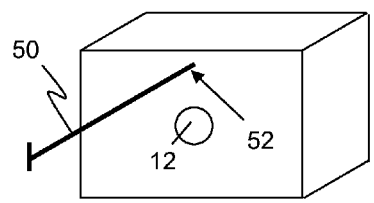
Figure 11D:
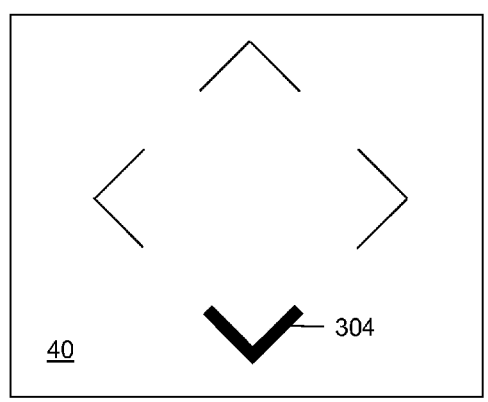
Figure 11E:
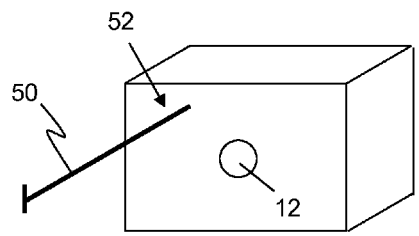
Figure 11F:
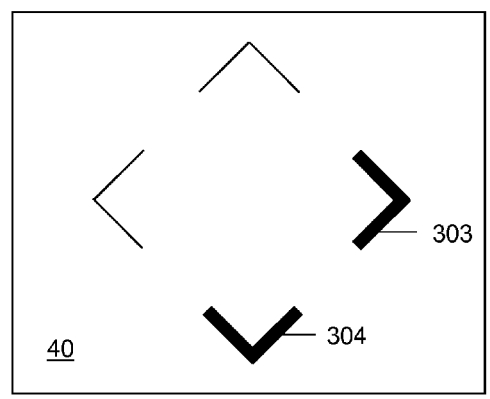

Referring now to FIG. 11A, proximal end 52 of needle 50 is shown at a position away from port 12 with respect to the x, y plane. In the situation depicted, proximal end 52 of needle 50 is to the right of port 12. As shown in corresponding FIG. 11B, display 40 may contain X, Y position indicators 301-304. In the situation depicted, left X, Y position indicator 301 is thicker, brighter, or the like to indicate to the user to move needle 50 such that proximal tip 52 moves left. In the situation depicted in FIGS. 11C and D, proximal end 52 of needle 50 is above port 12 in the X, Y plane and the down X,Y position indicator 304 is thicker, brighter, or the like, indicating to the use to move the needle 50 such that proximal tip 52 is lowered. In the situation depicted in FIG. 11E, the needle proximal tip 52 is up and to the right of port 12 in the X, Y plane. In corresponding FIG. 11F, the down and right position indicators 304, 303 are brighter, thicker, or the like to indicate that needle 50 should be moved down and to the right. It will be understood that any suitable numbers of X,Y position indicators may be employed and that any mechanism for indicating the direction in which needle should be moved may be employed. For example, and as shown in FIG. 11F, two or more indicators may light up to indicate desired movement in a diagonal direction; e.g. if the position of the proximal end of the needle is within +/−15 degrees of the midpoint between two indicators. Alternatively, an additional diagonal position indicator may be employed. The position indicators may be thickened, brightened, light up, blink, or otherwise provide an indication to a user as to which direction to move the needle.

Figure 12A:
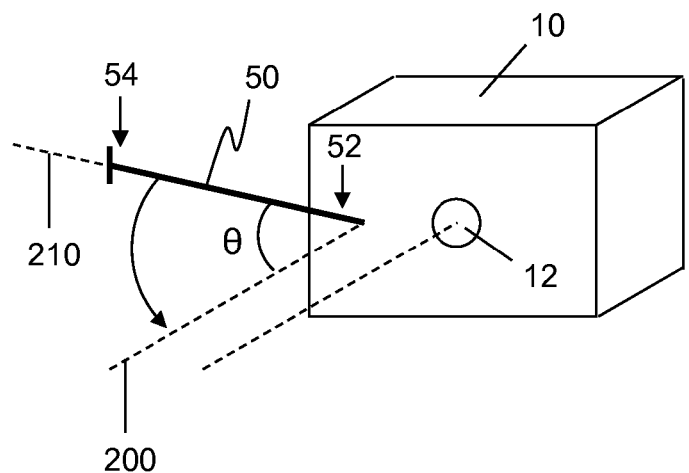
FIGS. 12A and C are schematic perspective views of representative implantable infusion devices.
Figure 12B:
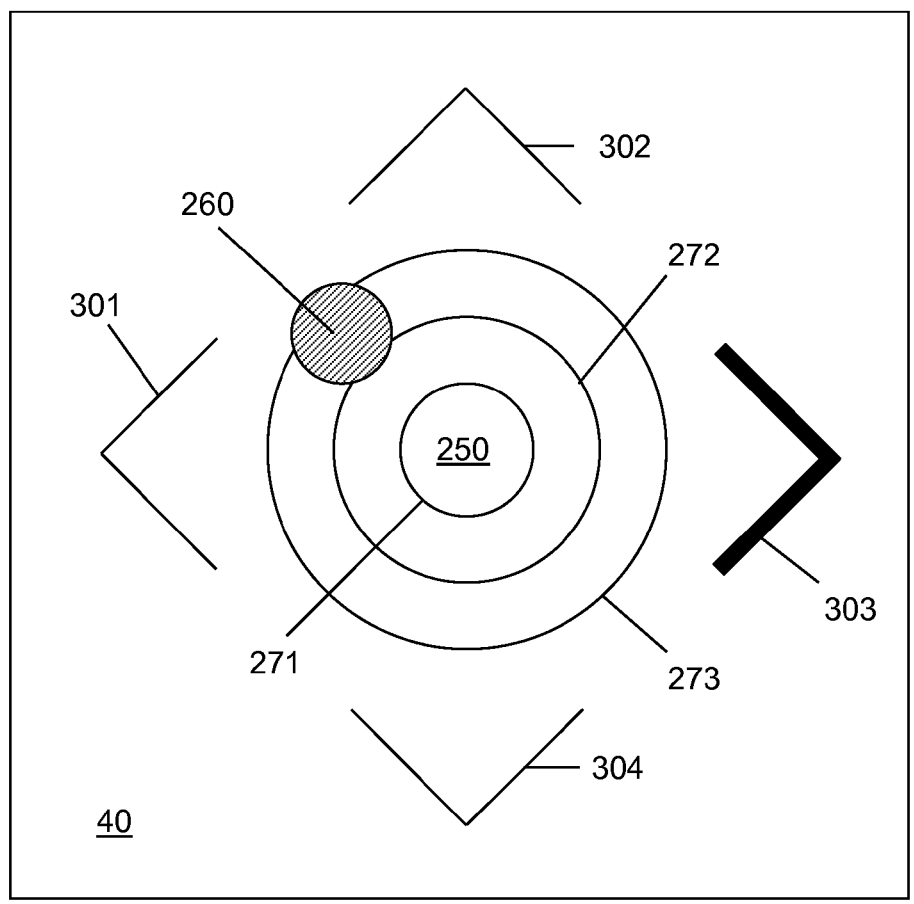
FIGS. 12B and D and FIG. 13 are schematic front views of a display graphically rendering a representative alignment of a needle with a port of an implantable infusion device.
Figure 12C:
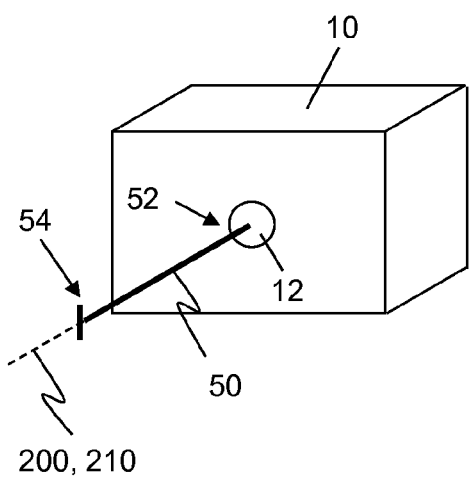
Figure 12D:
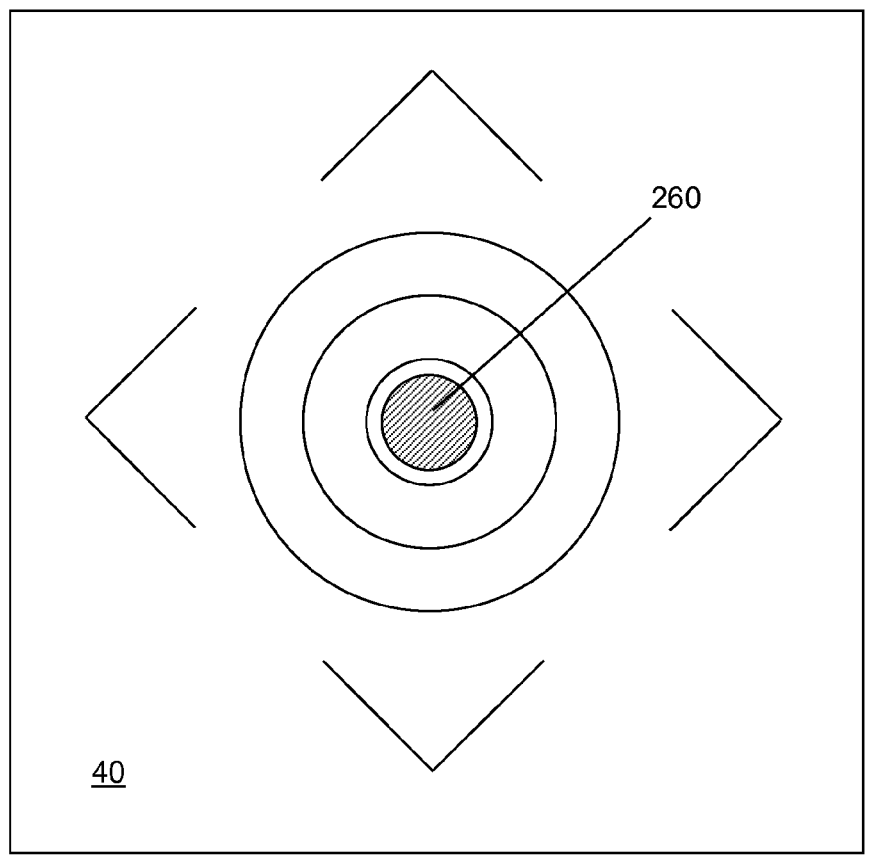

Referring now to FIG. 12A, a situation where needle 50 trajectory and X,Y position are not in the desired orientation and position is shown. Corresponding FIG. 12B shows a display 40 graphically depicting both an indication of desired movement to correct for X, Y position and tilt error, allowing user to appropriately move needle 50 to proper position and trajectory to align with port 12 (see FIG. 12C). After proper alignment of needle 50 with port 12, object 260 representing needle axis 210 occupies reference area 250 and X, Y position indicators are thinned, dimmed, turned off, or the like, indicating proper positioning an alignment (see FIG. 12D).

Figure 13:
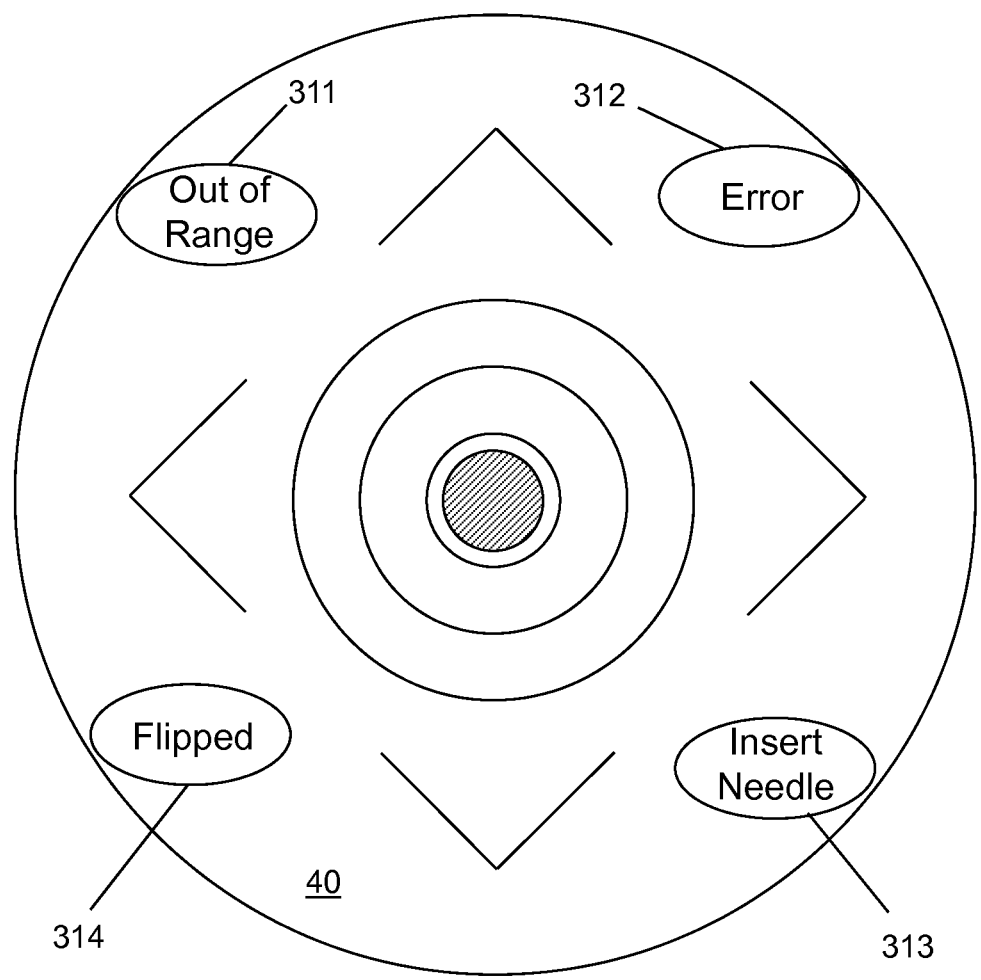

Referring to FIG. 13, additional features 311-314 that may be depicted on display 40 are shown. For example, when needle is properly positioned and aligned with port, an "insert needle" indicator 313 may appear. When tilt error of needle exceeds a defined threshold, e.g. 30 degrees, a "flipped" indicator 314 may appear. When the signal strength is not sufficient to perform navigational port finding, an "out of range" indicator 311 may appear. When an error occurs, an "error" indicator 312 may appear. When the device is turned on, an "on" indicator (not shown) may appear. Of course any other desired indicator may be graphically rendered on display 40.

It will be understood that the systems, components and devices described in FIGS. 1-13 are but examples of systems, components and devices that may be employed to detect relative orientation of a needle and a targeted port and that many other device or system configurations may be employed to carry out the methods described below. However, for the sake of convenience, the discussion that follows with regard to FIGS. 14-15 will refer to components as described with regard to FIGS. 1-13.

Figure 14:
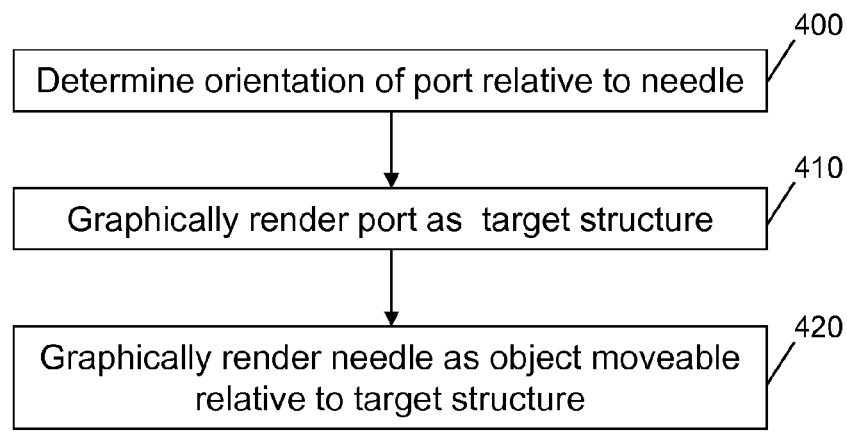
FIGS. 14-15 are flow diagrams of representative methods.

Referring to FIG. 14, a flow diagram of an illustrative method is shown. According to various embodiments, a method includes determining the orientation of a port 12 of an implantable infusion device 10 relative to a needle 50 for insertion into the port 12 (400). The determination (400) may be made by a processor 30 operably coupled to a receiver apparatus, such as a needle apparatus 20, that includes a port location signal receiver module 25 capable of receiving a signal from the infusion device 10 regarding the spatial orientation of the port 12. The processor 30 may obtain information regarding the location of the needle 50, including the proximal tip 52 and the distal end 54 or the actual needle trajectory axis 210. The relative alignment of the port 12 and the needle 50 may then be depicted on display 40 by graphically rendering the port 12 as a target structure having a reference area 250 (410) and by graphically rendering the needle as an object 260 moveable relative to the target structure (420). To graphically render the relative alignment, the processor 30 may be operably coupled to the display 40 and may be configured to cause the display 40 to graphically render the port 12 (the target structure) and the needle 50 (the object 260) and their relative alignment. When alignment is obtained, the object 260 occupies the reference area 250.

Figure 15:
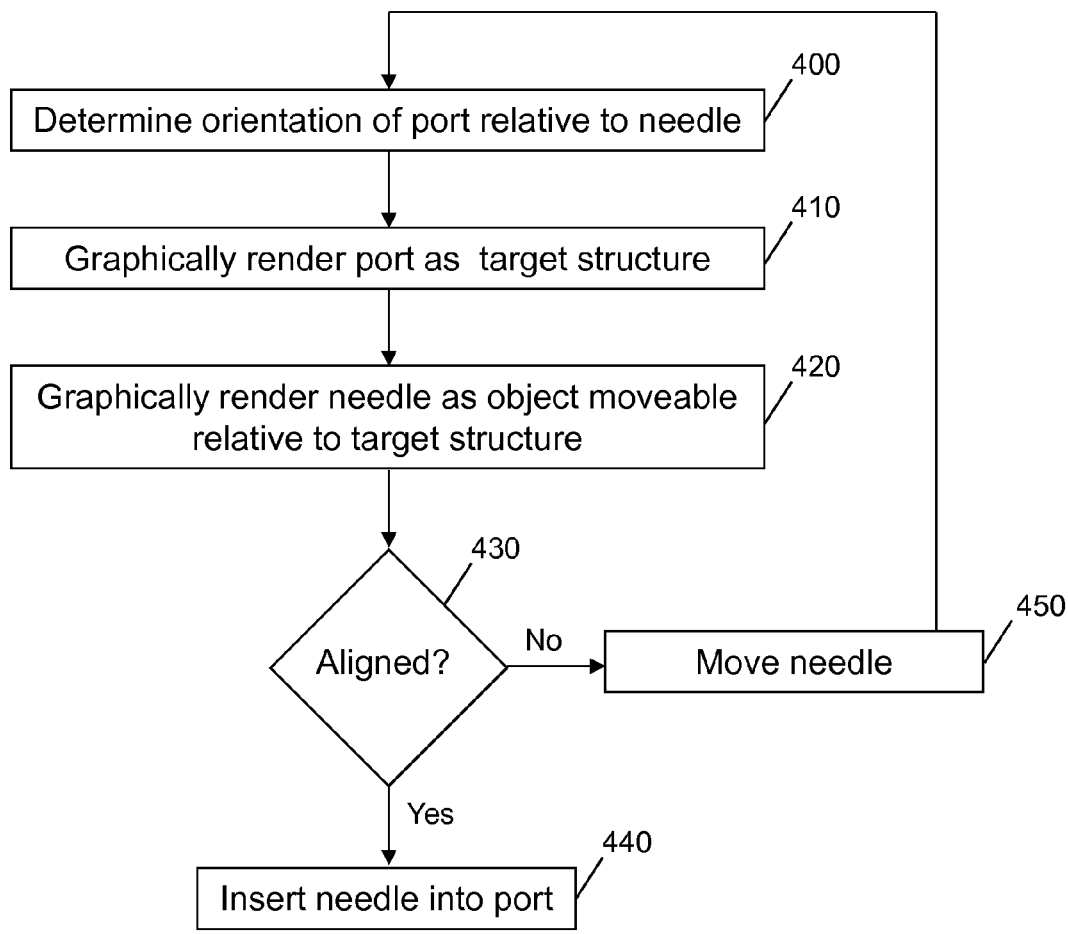

Referring now to FIG. 15, a user of the systems, devices and user-interfaces described herein may determine whether the needle is aligned with the port (430) by viewing the relative position of object 260 and reference area 250 graphically rendered on display 40. If aligned, the user may insert the needle 50 into the port 12 (440). If the needle 50 and port 12 are not aligned, the position or orientation of the needle 50 may be adjusted by the user (450). Steps 400, 410, and 420, as discussed above with regard to FIG. 14, will be performed as the needle position or orientation is adjusted (560). The user may continue adjusting the position or orientation of the needle 50 until alignment is achieved.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause a needle alignment medical device (or system including the medical device) to perform the methods described herein are contemplated. In an embodiment the computer readable medium contains instructions that when implemented cause an implantable medical device to (i) process information from a signal transmitted from an implantable infusion device regarding the location of a port of the infusion device; (ii) determine the orientation of a needle relative to the port based on the information from the transmitted signal; and (iii) graphically render relative alignment of the needle with the port, where the port is graphically rendered as a target structure having a reference area and the needle is graphically rendered as an object moveable relative to the target structure. Occupation of the reference area by the object indicates alignment of the port and the receiver apparatus.

Thus, embodiments of APPARATUS FOR ALIGNING NEEDLE WITH PORT OF INFUSION DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
   determining the orientation of a port of an implantable infusion device relative to a needle for insertion into the port, wherein the port has an axis defining a target trajectory for the needle and wherein the needle has a longitudinal axis;
   displaying a trajectory of the needle relative to the port by graphically rendering the axis of the port as a target structure having a reference area and by graphically rendering the longitudinal axis of the needle as an object moveable relative to the target structure;
   updating the graphical rendering of the longitudinal axis of the needle as the needle is being inserted into the port,
   wherein occupation of the reference area by the object indicates trajectory alignment of the axis of the port and the longitudinal axis of the needle.

2. The method of claim 1, wherein displaying relative alignment of the needle with the port further comprises graphically rendering one or more target trajectory reticules demarcating defined tilt errors.

3. The method of claim 2, wherein graphically rendering one or more target trajectory reticules demarcating defined tilt errors comprises graphically rendering the reticules as concentric circles, wherein the reference area comprises the center of the concentric circles.

4. A non-transitory computer-readable medium containing instructions that when implemented cause a needle alignment medical device system to:
   process information from a signal transmitted from an implantable infusion device regarding the location of a port of the infusion device, the port having an axis defining a target trajectory for a needle;
   determine the orientation of the needle relative to the port based on the information from the transmitted signal, wherein the needle has a longitudinal axis; and
   graphically render trajectory of the needle relative to the port, wherein the axis of the port is graphically rendered as a target structure having a reference area and the longitudinal axis of the needle is graphically rendered as an object moveable relative to the target structure;
   updating the graphical rendering of the longitudinal axis of the needle as the needle is being inserted into the port,
   wherein occupation of the reference area by the object indicates trajectory alignment of the axis of the port and the longitudinal axis of the needle.

5. A system for aligning a needle with a port of an implantable infusion device, the port having an axis defining a target trajectory for the needle and the needle having a longitudinal axis, the system comprising:
   a receiver apparatus having a port location signal receiver capable of receiving a signal from the implantable infusion device regarding spatial orientation of the port, wherein the receiver apparatus is configured to be fixed relative to the longitudinal axis of the needle as the needle is being inserted into the port;
   a processor operably coupled to the receiver apparatus and capable of determining the orientation of the axis of the needle relative to the axis of the port based on the received signal; and
   a display operably coupled to the processor,
   wherein the processor is configured to cause the display to graphically render a trajectory of the needle relative to the port, wherein the axis of the port is graphically rendered as a target structure having a reference area and the axis of the needle is graphically rendered as an object moveable relative to the target structure, wherein the processor is configured to update the graphical rendering of the axis of the needle as the needle is being inserted into the port, and wherein occupation of the reference area by the object indicates trajectory alignment of the port and the needle.

6. The system of claim 5, further comprising the implantable infusion device, wherein the implantable infusion device has a location signaling module capable of transmitting the signal regarding the orientation of the port.

7. The system of claim 5, wherein processor is further configured to cause the display to graphically render one or more target trajectory reticules demarcating defined tilt errors representing predetermined angular differences between the axis of the port and the axis of the needle.

8. The system of claim 7, wherein the trajectory reticules are concentric circles and wherein the reference area comprises the center of the concentric circles.

9. The system of claim 8, wherein at least a first and a second reticule are demarcated and a region is defined between the first and second reticule, the region representing between 5 degrees and 10 degrees of tilt error.

10. The system of claim 5, wherein at least a portion of the port location signal receiver module is disposed in a housing of the receiver apparatus, and wherein the display is disposed on or exposed through a surface of the housing.

11. The system of claim 10, wherein the processor is disposed in the housing.

* * * * *